United States Patent [19]
Kokubu et al.

[11] Patent Number: 6,028,119
[45] Date of Patent: Feb. 22, 2000

[54] PROCESS FOR METHANOL PRODUCTION

[75] Inventors: Yoshimitsu Kokubu, Osaka; Kenji Fujiwara, Hiroshima; Hiroshi Ono; Harushige Sugawara, both of Osaka; Kenichi Yamamoto, Hiroshima; Takeshi Oomatsuzawa, Yamaguchi; Masamitsu Inomata, Osaka, all of Japan

[73] Assignees: Mitsui Chemicals, Inc.; Petroleum Energy Center, both of Japan

[21] Appl. No.: 09/028,746

[22] Filed: Feb. 24, 1998

[30] Foreign Application Priority Data

Feb. 27, 1997 [JP] Japan .................................. 9-043289
Jan. 28, 1998 [JP] Japan .................................. 10-015381

[51] Int. Cl.[7] ............................. C07C 27/00; C07C 27/04
[52] U.S. Cl. ............................. 518/713; 518/700; 568/885
[58] Field of Search ................................... 518/700, 713; 568/885

[56] References Cited

U.S. PATENT DOCUMENTS 5,032,618  7/1991  Marchionna et al. .................. 518/700
5,045,520  9/1991  Hyde et al. .............................. 502/301

Primary Examiner—Paul J. Killos
Assistant Examiner—J. Parsa
Attorney, Agent, or Firm—Burns, Doane, Swecker & Mathis, L.L.P.

[57] ABSTRACT

Methanol is produced by reacting carbon monoxide and hydrogen in the presence of a Raney copper catalyst containing 80 to 99.9 wt. % of copper in a solvent. The catalysts employed in the present invention showed a much higher activity even under the conditions of a low temperature in methanol production, than any of the known catalysts. The process of the methanol production may eliminate necessity for recycling an unreacted synthesis gas into the reaction system, and makes it feasible to conduct methanol synthesis at a lower pressure than conventional processes.

9 Claims, No Drawings

PROCESS FOR METHANOL PRODUCTION

BACKGROUND OF THE INVENTION

1. Field of the Invention

The present invention relates to a novel process for methanol production. Methanol is an inexpensive and useful compound having a wide range of applications as an intermediate material for a variety of chemicals and as a solvent, a fuel for vehicles or a thermal power plant by itself.

2. Description of the Related Art

The process using carbon monoxide and hydrogen, the so-called vapor-phase method, had been industrially used for many years, for methanol production. For example, in 1913, BASF Inc., a German company, suggested that it may be possible to produce oxygen-containing compounds including methanol, from water gas at a temperature of at least 300° C. and a pressure of at least 100 atm., using a catalyst mainly containing an oxide of, e.g., Cr or Zn. Subsequently, the so-called high pressure methanol method had been initiated in many countries. In 1959, ICI Inc., a British company, setting in a high level of desulfurization technique of a synthesis gas, developed the so-called low pressure methanol method, where the reaction is conducted using a catalyst mainly containing CuO, at a lower temperature and a lower pressure than the previous method, i.e., at 200° to 300° C. and 50 to 150 atm. Then, there have been many improvements in catalysts and processes. Currently, most of processes of methanol production adapt a low pressure method at a reaction temperature of 200° C. and a reaction pressure of about 100 atm. In such a vapor-phase, low-temperature and low-pressure method, copper chromite has been used. It has been described that a Raney copper-zinc catalyst may be utilized as a copper catalyst for methanol production in a vapor phase. For example, *J. Catal.,*. 80, 1–13(1983) and *J. Catal.,* 80, 14–24(1983) have disclosed vapor-phase processes for methanol synthesis from carbon monoxide or carbon dioxide and hydrogen, using a Raney copper-zinc catalyst which can be prepared by developing a mother alloy containing 50 wt. % of aluminum, 30 to 36 wt. % of copper and 14 to 20 wt. % of zinc. They have described that a Raney copper catalyst containing zinc may have increased specific surface area, resulting in its improved activity.

Furthermore, Japanese Patent Laid-Open No. 197110/1995 has disclosed a continuous process for production of methanol, using a Raney copper alloy with a controlled particle size, prepared by adding and dispersing, on a disk rotating with a high speed, a melt of copper alloy consisting of 30 to 60 wt. % of copper, 0.5 to 25 wt. % of zinc and 0.5 to 10 wt. % of chromium or aluminum, and has described that its physical properties such as size distribution may not be changed even after 120 hours of the reaction.

There has been, however, a problem in these vapor-phase processes for methanol production that due to some problems in the process such as heat removal, it is difficult to scale up the process for inexpensively producing methanol in a large amount.

The reaction for methanol synthesis from carbon monoxide and hydrogen is exothermic as shown in the following equation and is an equilibrium reaction.

$$CO + 2H_2 \rightarrow CH_3OH \quad \Delta H_{298} = -21.7 \text{ kcal/mol}$$

A lower temperature and a higher pressure may be, therefore, favorable for methanol synthesis. A highly active catalyst at a lower temperature may be favorable because it may markedly improve the conversion rate of the raw material gases, eliminating necessity for recycling unreacted gases into the reaction system. Industrially, a catalyst highly active in methanol production at a lower pressure than that in a synthesis gas production, is extremely favorable because it can eliminate necessity of pressure elevation during introducing the synthesis gas into a reactor for methanol production. Recently, a low-temperature liquid-phase methanol synthesis has been of interest because reaction in a liquid phase may be effective in heat removal which is a problem in a vapor-phase method.

The prior art in this low-temperature liquid-phase methanol synthesis will be described.

There are known several catalysts active to some extent at a low temperature and a low pressure, e.g., below 160° C. and below 50 atm. Among others, copper or nickel catalysts are known to be highly active. It is, however, well known that a nickel catalyst may generate nickel carbonyl which is extremely toxic, making it very difficult to handle the catalyst.

For a copper catalyst, Japanese Patent Publication No. 51130/1988 has disclosed a synthesis of oxygen-containing compounds where carbon monoxide and hydrogen are reacted using a sodium or potassium alkoxide and a copper compound except copper oxides as catalysts. This publication has shown specific monovalent and bivalent copper compounds.

Japanese Patent Publication No. 2686/1994 (WO 86/03190) has disclosed a process for methanol production where in the presence of a catalyst consisting of a copper compound prepared according to Adkins method and an alkali metal alkoxide, carbon monoxide and hydrogen are reacted in a liquid phase, using a liquid reaction medium in the reactor comprising methanol and methyl formate as well as at least 50 vol. % of a nonpolar organic solvent having a lower dielectric constant than that of pure methanol at the same temperature. It has been described that the most suitable copper catalyst is copper chromite prepared by preliminary hydrogen reduction of a pyrolysis product of ammonium dichromate.

*Appl. Catal.,* 103, 105–122 (1993) has also disclosed similar copper-chromium catalysts, describing that for methanol synthesis from carbon monoxide and hydrogen, using a copper-chromite catalyst and potassium methoxide (or sodium methoxide) may reduce the reaction temperature by about 100° C., resulting in significant reduction in the amount of the recycle gas.

U.S. Pat. Nos. 4,992,480 and 4,935,395 have disclosed a process for methanol production from a synthesis gas using a homogeneous catalyst consisting of an alkoxide and a carbonyl compound of metal selected from the group consisting of Cu, Ni, Pd, Co, Ru, Mo and Fe.

As far as we have verified it, there have been no catalysts with an adequate activity for low-temperature liquid-phase methanol synthesis. Specifically, a copper catalyst having some valence including copper chromite catalysts such as copper chromite may be subject to reduction and conversion of the copper oxide on the surface into metal copper, resulting in significant deterioration of its activity. Carbonyl compounds have some problems such as difficulty in handling, and thus cannot be used in an industrial scale.

A metal alkoxide is essential for producing methanol at a low temperature and a low pressure. It has been found that a part of the metal alkoxide used is lost by conversion into a formate during the reaction. It has been also found that the converted amount may be increased with increase of the metal alkoxide. Thus, the metal alkoxide should be used in a substantially less amount than that known in the prior art; otherwise, the process may be quite uneconomical.

On the other hand, use of methanol as a solvent may be very advantageous because it can eliminate separation of the product from the solvent. All the catalysts for low-temperature, liquid-phase methanol synthesis have a poor activity in methanol which is also the product. Even when used in another solvent system, these catalysts may be subject to deterioration in their activity due to methanol sequentially produced. Therefore, there has been a strong demand to obtain a catalyst which is little deteriorated at a low temperature and a low pressure in the presence of methanol and is highly active with a low concentration of a metal alkoxide.

SUMMARY OF THE INVENTION

It is an objective of the present invention to provide a highly active and long-lived catalyst for methanol production from carbon monoxide and hydrogen at a low temperature and a low pressure in the presence of a solvent.

We have intensively explored a catalyst showing a high activity in a batch or flow reaction under the conditions of a high concentration of methanol and a low concentration of a metal alkoxide. Then, we have surprisingly observed that among copper catalysts, a Raney copper catalyst can produce methanol at a specifically high rate. We have also observed that a Raney copper catalyst containing calcium is not only highly active but also little deteriorated, and may be stable in its activity.

The present invention provides a process for methanol production, where carbon monoxide and hydrogen are reacted in the presence of a metal alkoxide and a Raney copper in which the copper content is in the range of 80.0 to 99.9 wt. %, in a solvent.

According to the process of the present invention for methanol production, methanol is continuously produced by reacting carbon monoxide and hydrogen, using a Raney copper and a metal alkoxide as catalysts. Even under the conditions of a low temperature, a low pressure and a low concentration of the metal alkoxide, the catalysts showed a much higher activity in methanol production, than any of the known catalysts, as compared in their space time yields described later, and provided stable results for 75 hours. It may, thus, eliminate necessity for recycling an unreacted synthesis gas into the reaction system. The process may make it feasible to conduct methanol synthesis at a lower pressure than that in preparation of a synthesis gas to eliminate necessity for elevating the synthesis gas pressure. Therefore, the process is industrially advantageous.

DETAILED DESCRIPTION OF THE PREFERRED EMBODIMENTS

The present invention will be described in detail.

A Raney copper used in the process of the present invention is a copper catalyst mainly containing essentially zero (0) valent copper, prepared by developing a mother alloy comprising copper and aluminum with, e.g., an aqueous alkaline solution. The mother alloy may be blocks prepared by crushing or powders. The Raney copper preferably contains calcium in addition to copper and aluminum. The calcium content lower than 0.01 wt. % may lead to an inadequate effect, while that higher than 20 wt. % may reduce the content of the active copper component. The content is, therefore, preferably 0.01 to 20 wt. %, more preferably 0.05 to 15 wt. %, and most preferably 0.1 to 10 wt. %.

The Raney copper catalyst may contain, in addition to copper, aluminum and calcium, group VIIIA metals such as cobalt and nickel; group VIIA metals such as manganese and rhenium; group VIA metals such as chromium and molybdenum; group VA metals such as vanadium and niobium; group IVA metals such as titanium and zirconium; group IB metals such as gold and silver; and group IIB metals such as zinc and cadmium. These 4th metals may be effectively added in combination. The amount of the 4th metal may be generally, but not limited to, 0.01 to 20 wt. %. A Raney copper other than those described above may be used without restricting the present invention.

The Raney copper used in the present invention can be prepared by developing a mother alloy, which may be conducted according to a known process. For example, the aqueous alkaline solution used in the development of the mother alloy may be an aqueous solution of sodium or potassium hydroxide or carbonate. In the light of economical efficiency, a sodium hydroxide aq. is preferable. The amount of the alkali is generally 1 to 20 mol, preferably 1.5 to 15 mol, and more preferably 2 to 10 mol, to one mol of aluminum in the alloy. The aqueous alkaline solution may have a concentration of 10 to 40 wt. %. If the concentration is lower than 10 wt. %, the mother alloy may not be sufficiently developed to achieve an adequate activity of the catalyst. A development temperature of the mother alloy and a maturing temperature may vary depending on the type of the alkali used, but they may be generally 20° to 100° C. The temperatures lower than 20° C. may cause a reduced rate of aluminum elution, leading to insufficient development and thus an inadequate activity. The addition rate of the mother alloy may vary depending on the amount of the mother alloy to be developed, but it may be preferably added within 0.5 to 1 hours. When added more quickly, development may be accelerated too much to control the development temperature, while when more slowly, the catalyst may become undesirably heterogeneous. A maturing period for the Raney copper may depend on the type of the alkali used, but preferably 0.5 to 6 hours. When shorter than 0.5 hours, aluminum may be insufficiently eluted, resulting in an inadequate activity, while the period longer than 6 hours may have no significance because the reaction will be completed within 6 hours. The content of copper in the Raney copper catalyst prepared as described above is generally 80.0 to 99.9 wt. % and preferably 90.0 to 99.9 wt. %. The content beyond the range of 80.0 to 99.9 wt. % may cause an inadequate activity of the catalyst. In addition, it is preferable that the Raney copper has a high specific surface area as measured by BET method; generally at least 5 $m^2/g$.

The amount of the Raney copper used in the process of the present invention may depend on that of the solvent. The Raney copper may be adequately effective in a small amount, and the excessive amount may cause insufficient stirring, resulting in reduction in its activity. The amount of the Raney copper is, therefore, 0.5 to 80 wt. %, preferably 1 to 70 wt. %, to that of the solvent.

The metal alkoxide used in the process of the present invention is at least one alkoxide of metal selected from the group consisting of alkali metals such as Li, Na and K, and alkaline earth metals such as Mg, Ca and Sr, preferably K and Na. The alkoxide moiety has 1 to 10 carbon atoms; preferably methoxide, ethoxide, propoxide and butoxide, more preferably methoxide. Metal alkoxides preproduced by reacting a metal hydride and an alcohol may be used.

The amount of the metal alkoxide used in the process of the present invention may be appropriately determined in the light of the amounts of the Raney copper and the solvent. A too small amount of metal alkoxide to the Raney copper may cause a poor effect of the catalyst, while an excessive amount may inhibit the catalyst effect. The amount of the metal alkoxide is, therefore, 0.01 to 100 times, preferably 0.1 to 30 times, more preferably 0.1 to 10 times, to that of the Raney copper by weight. An excessive amount of the metal alkoxide to the solvent may not only cause inadequate stirring of the reaction system, but also increase loss of the alkoxide during the reaction, which is economically undesirable, while a too small amount may lead to a poor activity of the catalyst. The amount of the metal alkoxide is, therefore, 0.01 to 10 wt. % to that of the solvent.

Solvents used in the process of the present invention may be methanol or a mixed solvent of methanol and a co-solvent or co-solvents. Suitable co-solvents, generally include, but not limited to, ethers such as dioxane, tetrahydrofuran, diethyl ether and diphenyl ether; glymes such as monoglyme and diglyme and triglyme; esters such as methyl acetate and ethyl propionate; alcohols with up to 6 carbons such as ethanol, propanol and hexanol; hydrocarbons such as hexane, benzene, decalin and chlorobenzene; and halogenated hydrocarbons. A protic polar solvents such as dimethylformamide and N-methylpyrrolidone may be used as the co-solvent. Among these co-solvents, ethers such as dioxane and tetrahydrofuran are preferable in terms of the activity of the catalyst. There are no limitations for the proportion of methanol in the mixed solvent; methanol may be contained at the concentration of more than 5 wt. % without any reduction of the activity. In the light of aspects related to the process such as separation from the product, use of pure methanol is particularly preferable.

The Raney copper and the metal alkoxide used in the process of the present invention may be mixed prior to their use, or may be sequentially added into the solvent. In either way, they can be effective as a catalyst for methanol synthesis.

The process of the present invention uses a catalyst having an excellent activity in methanol synthesis even at a low temperature below 160° C., and can be conducted at a temperature in the range of 40° to 200° C. When the reaction temperature is higher than 200° C., the conversion rate may be markedly reduced, while when lower than 40° C., the reaction rate may be impractically low. It is preferably in the range of 60° to 180° C., more preferably 80° to 160° C. However, this range does not limit the present invention, and a temperature beyond the range may be employed, in the light of comprehensive economical efficiency including recovery of reaction heat.

The raw materials, carbon monoxide and hydrogen, may contain nitrogen and carbon dioxide, but the less carbon monoxide the better. It is preferable that sulfur compounds and moisture are removed to a trace amount prior to initiation of methanol synthesis. Blending ratio of carbon monoxide and hydrogen may be 1:0.5 to 1:5. When the ratio of hydrogen to carbon monoxide is higher than 2, i.e., the stoichiometric ratio, selectivity for methanol may be improved, but a significantly high ratio may be uneconomical because excessive hydrogen remains unreacted. In practical, the ratio is preferably 1:1.5 to 1:2.5.

In the process of the present invention, the higher the reaction pressure is, the higher the activity for methanol synthesis is. The pressure may be practically up to 120 kg/cm$^2$-G. for supplying the synthesis gas into the reactor without elevation of its pressure. However, the process of the present invention may be conducted at a pressure of higher than the value.

The process of the present invention can be effective in both batch and flow reactions.

The following examples will describe the present invention more specifically.

1. Tests of catalyst activity and life in a flow reaction

EXAMPLE 1

In a container was weighed 90 g of copper alloy powder for Raney alloy (product of Kishida Chemical). The powder was portion wise added to 556 g of 24 wt. % sodium hydroxide aq. in a reactor sealed with nitrogen, and then the copper alloy powder was developed over 1 hour, maintaining the liquid temperature at 55°±2° C. After the addition, the reaction was matured by maintaining the temperature at 45° C. for an additional one hour. The resultant powder was fully washed with deoxidized distilled water batchwise until pH of supernatant became 8.7 to 9.0. After the solvent was replaced with dried methanol, the resultant powder was dried in an atmosphere of nitrogen to provide 43 g of a Raney copper catalyst. Analysis indicated that the catalyst consisted of 98.5 wt. % of copper and 0.99 wt. % of aluminum. Its specific surface area was 15.9 m$^2$/g.

In a 260 mL flow reactor were placed 37.2 g of the above Raney copper catalyst and 80 mL of 2 wt. % potassium methoxide in methanol in an atmosphere of nitrogen. Introducing a synthesis gas of CO/H$_2$=1/2 (molar ratio) at room temperature, a continuous reaction was initiated at a constant pressure of 50 kg/cm$^2$-G. and a temperature of 120° C., during which a solution of 2 wt. % potassium methoxide in methanol was continuously supplied into the reactor at a rate of 15 mL/hr. Furthermore, a part of the supplied gas was removed as unreacted gas, while a part of the reaction liquid was removed at regular time intervals to maintain the liquid surface at a constant level. Analysis indicated the reaction results that CO conversion rate and methanol selectivity were 97.9% and 94.4%, respectively and the catalyst activity was stable for 75 hours. During the reaction, an average yield of methanol [STY (space time yield)] on the basis of the solvent was 160 g-MeOH/L/hr.

The appearance of the catalyst was changed from black to dark reddish-brown after the reaction. Analysis indicated that its BET specific surface area was slightly reduced to 10.9 m$^2$/g.

EXAMPLE 2

A mother alloy was prepared according to the process described in Japanese Patent Laid-Open No 172366/1989, the so-called "rotating-water atomizing method". Specifically, 100 g of copper-aluminum alloy (Cu/Al=50/50) was melted at about 1,000° C. in a high-frequency melting furnace. Then, metal calcium was added and melted to 1.2 wt. % to the alloy. The melted alloy was sprayed into rotating water to be quenched and solidified to give Cu-Al-Ca alloy powder.

In a container was weighed 90 g of the above copper alloy powder containing calcium. The powder was portion wise added to 556 g of 24 wt. % sodium hydroxide aq. in a reactor sealed with nitrogen, and then the powder was developed over 1 hour, maintaining the liquid temperature at 55°±2° C. After the addition, the reaction was matured by maintaining the temperature at 45° C. for an additional one hour. The resultant powder was fully washed with deoxidized distilled water batchwise until pH of supernatant became 8.7 to 9.0. After the solvent was replaced with dried methanol, the resultant powder was dried in an atmosphere of nitrogen to provide 43 g of a Raney copper catalyst containing calcium. Analysis indicated that the catalyst consisted of 97.5 wt. % of copper, 1.01 wt. % of aluminum and 1.0 wt. % of calcium. Its specific surface area was 25.8 m$^2$/g.

A reaction was conducted as described in Example 1, except that 37.2 g of the above Raney copper catalyst was used.

Analysis indicated the reaction results that CO conversion rate and methanol selectivity were 98.1% and 96.5%, respectively and that the catalyst activity was stable for 75 hours. During the reaction, an average yield of methanol [STY (space time yield)] on the basis of the solvent was 170 g-MeOH/L/hr.

The appearance of the catalyst was not changed (black) after the reaction. Analysis indicated that its BET specific surface area was 25.3 m$^2$/g.

Comparative Example 1

A reaction was conducted as described in Example 1, except that the Raney copper catalyst was replaced with a commercially available copper-chromite catalyst (Product of Nissan Girdler Catalyst Co., Ltd.). The catalyst showed a maximum activity of 58 g-MeOH/L/hr at 10 hours of the reaction, but gradually lost its activity, giving unstable results. Thus, the reaction was quenched at 25 hours. At the end of this reaction, precipitation of copper mirror was observed due to reduction of copper during the reaction.

EXAMPLE 3

A reaction was conducted as described in Example 1, except that the amount of the Raney copper catalyst was 50 g, to give the reaction results that CO conversion rate and methanol selectivity were 98.3% and 95.5%, respectively. An average STY was 225 g-MeOH/L/hr.

EXAMPLE 4

A reaction was conducted as described in Example 1, except that potassium methoxide was replaced with sodium methoxide, to give the reaction results that CO conversion rate and methanol selectivity were 97.1% and 94.3%, respectively. An average STY was 148 g-MeOH/L/hr.

EXAMPLE 5

A reaction was conducted as described in Example 1, except that the concentration of potassium methoxide was changed from 2 wt. % to 1.5 wt. %, to give the reaction results that CO conversion rate and methanol selectivity were 94.8% and 93.1%, respectively. An average STY was 135 g-MeOH/L/hr.

2. Tests of catalyst activity in a batch reaction

EXAMPLE 6

In an autoclave were placed 1 g of the Raney copper catalyst obtained in Example 1, 2.1 g (30 mmol) of potassium methoxide and 20 mL of methanol, and a synthesis gas of CO/H$_2$=1/2 (molar ratio) was introduced at room temperature. The reaction was conducted at 120° C. and 50 kg/cm$^2$-G. Confirming that the reaction pressure was reduced to 9 kg/cm$^2$-G. after about 45 min., the reaction was quenched. Analysis indicated that a STY on the basis of the solvent used was 198 g-MeOH/L/hr.

EXAMPLE 7

A reaction was conducted as described in Example 6, except that the Raney copper catalyst obtained in Example 1 was replaced with 1 g of the Raney copper catalyst containing calcium obtained in Example 2. Confirming that the reaction pressure was reduced to 8.5 kg/cm$^2$-G. after about 45 min., the reaction was quenched.

Analysis indicated that a STY on the basis of the solvent used was 205 g-MeOH/L/hr.

EXAMPLE 8

A reaction was conducted as described in Example 6, except that the amount of potassium methoxide was changed from 2.1 g (30 mmol) to 0.14 g (2 mmol). Confirming that the reaction pressure was reduced to 10.5 kg/cm$^2$-G. after about 45 min., the reaction was quenched. Analysis indicated that a STY on the basis of the solvent used was 178 g-MeOH/L/hr.

EXAMPLE 9

A reaction was conducted as described in Example 6, except that the solvent, methanol, was replaced with tetrahydrofuran. Confirming that the reaction pressure was reduced to 8 kg/cm$^2$-G. after about 45 min., the reaction was quenched. Analysis indicated that a STY on the basis of the solvent used was 212 g-MeOH/L/hr.

EXAMPLE 10

A reaction was conducted as described in Example 6, except that the solvent, methanol, was replaced with a mixture of 5 wt. % of methanol and 95 wt. % of dioxane. Confirming that the reaction pressure was reduced to 8.5 kg/cm$^2$-G. after about 45 min., the reaction was quenched. Analysis indicated that a STY on the basis of the solvent used was 189 g-MeOH/L/hr.

EXAMPLE 11

The amount of 24 wt. % sodium hydroxide aq. used in development of the mother alloy was changed from 556 g to 228 g, to give 90 wt. % of the copper content in the Raney copper catalyst. A reaction was conducted as described in Example 6, except that the Raney copper catalyst thus obtained was used. Analysis indicated that a STY on the basis of the solvent used was 173 g-MeOH/L/hr.

EXAMPLE 12

As in Example 2, 100 g of copper-aluminum alloy (Cu/Al=50/50) was melted at about 1,000° C. in a high-frequency melting furnace. Then, metal calcium was added and melted to 17 wt. % to the alloy. The melted alloy was sprayed into rotating water to be quenched and solidified to give Cu-Al-Ca alloy.

The alloy obtained was developed with alkali as described in Example 2 to give 42.5 g of a Raney copper catalyst consisting of 83.1 wt. % of copper, 0.98 wt. % of aluminum and 15.0 wt. % of calcium. Its specific surface area was 32.3 m$^2$/g.

A reaction was conducted as described in Example 6, except that the Raney copper catalyst containing calcium thus obtained was used.

Analysis indicated that a STY on the basis of the solvent used was 213 g-MeOH/L/hr. The appearance of the catalyst was not changed(black). Analysis indicated that its BET specific surface area was 30.9 m$^2$/g.

EXAMPLE 13

As in Example 2, 100 g of copper-aluminum alloy (Cu/Al=50/50) was melted at about 1,000° C. in a high-frequency melting furnace. Then, metal calcium was added and melted to 0.01 wt. % to the alloy. The melted alloy was sprayed into rotating water to be quenched and solidified to give Cu-Al-Ca alloy.

The alloy obtained was developed with alkali as described in Example 2 to give 42 g of a Raney copper catalyst consisting of 99.1 wt. % of copper, 0.78 wt. % of aluminum and 0.008wt. % of calcium. Its specific surface area was 17.0 $m^2/g$.

A reaction was conducted as described in Example 6, except that the Raney copper catalyst containing calcium thus obtained was used.

Analysis indicated that a STY on the basis of the solvent used was 198 g-MeOH/L/hr. The appearance of the catalyst was changed from black to dark reddish-brown. Analysis indicated that its BET specific surface area was slightly reduced to 12.9 $m^2/g$.

Comparative Example 2

A reaction was conducted as described in Example 6, except that the Raney copper catalyst and methanol as the solvent were replaced with 1 g (10 mmol) of CuCl and tetrahydrofuran, respectively. Confirming that the reaction pressure was reduced to 19 $kg/cm^2$-G. after about 60 min., the reaction was quenched. Analysis indicated that a STY on the basis of the solvent used was 78 g-MeOH/L/hr. At the end of this reaction, precipitation of copper mirror was observed due to reduction of copper during the reaction.

Comparative Example 3

A reaction was conducted as described in Example 8, except that the Raney copper catalyst was replaced with 1 g of copper chromite. In this reaction, some pressure reduction was observed, and the catalyst showed little activity for methanol. At the end of this reaction, precipitation of copper mirror was observed due to reduction of copper during the reaction.

Comparative Example 4

A reaction was conducted as described in Example 8, except that the Raney copper catalyst was replaced with 1 g (10 mmol) of CuCl. In this reaction, some pressure reduction was observed, and the catalyst showed little activity for methanol. At the end of this reaction, precipitation of copper mirror was observed due to reduction of copper during the reaction.

Comparative Example 5

A reaction was conducted as described in Example 8, except that the Raney copper catalyst was replaced with 2.6 g (10 mmol) of molybdenum hexacarbonyl ($Mo(CO)_6$) prepared according to the process described in U.S. Pat. No. 4,623,634. Analysis indicated that a STY on the basis of the solvent used was 56 g-MeOH/L/hr. A large amount of molybdenum hexacarbonyl was adhered to the upper surface of the autoclave.

Comparative Example 6

A reaction was conducted as described in Example 8, except that the Raney copper catalyst was replaced with 1 g (10 mmol) of CuCl and the solvent, methanol, was replaced with a mixture of 5 wt. % methanol and 95 wt. % dioxane. Analysis indicated that a STY on the basis of the solvent used was 32 g-MeOH/L/hr.

Reference Example 1

A Raney copper catalyst containing 25 wt. % of aluminum was prepared as Example 1, except that 556 g of 24 wt. % sodium hydroxide aq. was replaced with 228 g of 15 wt. % sodium hydroxide aq. A reaction was conducted as described in Example 6, using the Raney copper catalyst thus obtained. Analysis indicated that a STY on the basis of the solvent used was 88 g-MeOH/L/hr.

Comparative Example 7

A reaction was conducted as described in Example 6, except that the Raney copper catalyst was replaced with a Raney copper-zinc-chromium consisting of 77.6 wt. % of copper, 8.4 wt. % of aluminum, 10.4 wt. % of zinc and 3.6 wt. % of chromium (product of Nikko Rika, K.K.). In this reaction, some pressure reduction was observed, and the catalyst showed little activity for methanol.

Comparative Example 8

A reaction was conducted as described in Example 6, except that the Raney copper catalyst was replaced with copper powder with a specific surface area of 1.2 $m^2/g$ (Mitsui Mining & Smelting, "1050Y"). In this reaction, some pressure reduction was observed, and the catalyst showed little activity for methanol.

The results obtained in the above Examples and Comparative Examples are summarized in Tables 1 and 2.

TABLE 1

Tests of catalyst activity and life in a flow reaction

| Exam. No. | Catalyst | Co-catalyst | Supplement | Results*[3] |
|---|---|---|---|---|
| Ex.1 | Raney copper*[1] (37.2 g) | KOMe (18 mmol) | KOMe/MeOH (2 wt.%, 15 mL/h) | STYav(g/L/h)160 COconv.(%)97.9 MeOHsel.(%)94.4 |
| Ex.2 | Raney copper*[2] (37.2 g) | ↑ | ↑ | STYav(g/L/h)170 COconv.(%)98.1 MeOHsel.(%)96.5 |
| Comp. Ex.1 | Copper chromite (37.2 g) | ↑ | ↑ | STYmax(g/L/h)58 |
| Ex.3 | Raney copper*[1] (50 g) | ↑ | ↑ | STYav(g/L/h)225 COconv.(%)98.3 MeOHsel.(%)95.5 |
| Ex.4 | Raney copper*[1] (37.2 g) | NaOMe (18 mmol) | ↑ | STYav(g/L/h)148 COconv.(%)97.1 MeOHsel.(%)94.3 |
| Ex.5 | ↑ | KOMe (18 mmol) | KOMe/MeOH (1.5 wt.%, 15 mL/h) | STYav(g/L/h)135 COconv.(%)94.8 MeOHsel.(%)93.1 |

*[1]Copper: 98.5 wt.%; Aluminum: 0.99 wt.%
*[2]Copper: 97.5 wt.%; Aluminum: 1.01 wt.%; Calcium: 1.0 wt.%
*[3]STYmax: Maximum STY(g-MeOH/L/h);
STYav: Average STY (g-MeOH/L/h);
COconv.: CO conversion rate (%);
MeOHsel.: Methanol selectivity (%).
Conditions; Temperature: 120° C.,
Pressure: 50 $kg/cm^2$-G.,
$H_2/CO$ = 2.

TABLE 2

Tests of catalyst activity in a batch reaction

| Exam. No. | Catalyst | Co-catalyst | Solvent | STY (g/L/h) |
|---|---|---|---|---|
| Ex.6 | Raney copper*1 (1 g) | KOMe (30 mmol) | MeOH (20 ml) | 198 |
| Ex.7 | Raney copper*2 (1 g) | ↑ | ↑ | 205 |
| Ex.8 | Raney copper*1 (1 g) | KOMe (2 mmol) | ↑ | 178 |
| Ex.9 | ↑ | KOMe (30 mmol) | THF*8 (20 ml) | 212 |
| Ex.10 | ↑ | ↑ | MeOH/Dioxane (5/95, 20 ml) | 189 |
| Ex.11 | Raney copper*3 (1 g) | ↑ | MeOH (20 ml) | 178 |
| Ex.12 | Raney copper*4 (1 g) | ↑ | ↑ | 213 |
| Ex.13 | Raney copper*5 (1 g) | ↑ | ↑ | 198 |
| Comp. Ex.2 | CuCl (1 g, 10 mmol) | ↑ | THF (20 ml) | 78 |
| Comp. Ex.3 | Copper chromite (1 g) | ↑ (2 mmol) | MeOH (20 ml) | trace |
| Comp. Ex.4 | CuCl (1 g, 10 mmol) | ↑ | ↑ | trace |
| Comp. Ex.5 | Mo(CO)$_6$ (10 mmol) | ↑ | ↑ | 56 |
| Comp. Ex.6 | CuCl (1 g, 10 mmol) | ↑ | MeOH/Dioxane (5/95, 20 ml) | 32 |
| Ref. Ex.1 | Raney copper*6 (1 g) | ↑ (30 mmol) | MeOH (20 ml) | 88 |
| Comp. Ex.7 | Raney copper*7 (1 g) | ↑ | ↑ | trace |
| Comp. Ex.8 | Copper powder (1 g) | ↑ | ↑ | trace |

*1 Cu: 98.5 wt.%, Aluminum: 0.99 wt.%
*2 Cu: 97.5 wt.%, Aluminum: 1.01 wt.%, Calcium: 1.0 wt.%
*3 Cu: 90.0 wt.%
*4 Cu: 83.1 wt.%, Aluminum: 0.98 wt.%, Calcium: 15.0 wt.%
*5 Cu: 99.1 wt.%, Aluminum: 0.78 wt.%, Calcium: 0.008 wt.%
*6 Cu: 75.0 wt.%, Aluminum: 25.0 wt.%,
*7 Cu: 77.6 wt.%, Aluminum: 8.4 wt.%, Zinc: 10.4 wt.%, Chromium: 3.6 wt.%
*8 THF: Tetrahydrofuran
Conditions; Temperature: 120° C., Pressure: 50 kg/cm$^2$-G., H$_2$/CO = 2

What is claimed is:

1. A process for methanol production, wherein carbon monoxide and hydrogen are reacted in the presence of a metal alkoxide and a Raney copper catalyst in which copper content is in the range of 80.0 to 99.9 wt. %, in a solvent.

2. A process as claimed in claim 1, wherein the Raney copper catalyst contains calcium.

3. A process as claimed in claim 2, wherein the calcium content in the Raney copper catalyst is in the range of 0.01 to 20 wt. %.

4. A process as claimed in claim 1, wherein the metal alkoxide is an alkali metal alkoxide or an alkaline-earth metal alkoxide.

5. A process as claimed in claim 4, wherein the metal alkoxide is potassium methoxide or sodium methoxide.

6. A process as claimed in claim 1, wherein the solvent is methanol or a mixed solvent of at least 5 wt. % of methanol and a remaining co-solvent.

7. A process as claimed in claim 1, wherein the concentration of the metal alkoxide is in the range of 0.01 to 10 wt. % to the solvent.

8. A process as claimed in claim 1, wherein the reaction is conducted at a temperature in the range of 60° to 180° C.

9. A process as claimed in claim 1, wherein the reaction is conducted under a pressure in the range of 10 to 120 atm.

\* \* \* \* \*